US00PP36521P2

(12) United States Plant Patent
Westervelt

(10) Patent No.: US PP36,521 P2
(45) Date of Patent: Mar. 4, 2025

(54) ***MACLURA* PLANT NAMED 'Hibbard'**

(50) Latin Name: *Maclura pomifera*
Varietal Denomination: Hibbard

(71) Applicant: Keith D. Westervelt, Manhattan, KS (US)

(72) Inventor: Keith D. Westervelt, Manhattan, KS (US)

( * ) Notice: Subject to any disclaimer, the term of this patent is extended or adjusted under 35 U.S.C. 154(b) by 0 days.

(21) Appl. No.: 18/797,429

(22) Filed: Aug. 7, 2024

(51) Int. Cl.
*A01H 6/00* (2018.01)
*A01H 5/02* (2018.01)

(52) U.S. Cl.
USPC ..... Plt./216

(58) Field of Classification Search
USPC ..... Plt./216
CPC ..... A01H 6/00; A01H 5/02
See application file for complete search history.

*Primary Examiner* — Keith O. Robinson
(74) *Attorney, Agent, or Firm* — Penny J. Aguirre

(57) ABSTRACT

A new cultivar of *Maclura* tree named 'Hibbard' that is characterized by its rapid growth habit, an average of 60 cm a year, its lack of fruit production, its large glossy foliage, and its thornless branches.

2 Drawing Sheets

Botanical classification: *Maclura pomifera.*
Variety denomination: 'Hibbard'.

BACKGROUND OF THE INVENTION

The present invention relates to a new and distinct cultivar of *Maclura pomifera* and will be referred to hereafter by its cultivar name, 'Hibbard'. 'Hibbard' is a new cultivar of Osage orange tree grown for use as a landscape plant.

The Inventor discovered the new cultivar, 'Hibbard' as a chance seedling that was found growing at a residence in Wamego, Kansas in August of 2017. The parents are therefore unknown.

Asexual propagation of the new cultivar was first accomplished by hot scion grafting onto *Maclura pomifera* root stook under the direction of the Inventor in McMinnville, Oregon in January of 2018. Asexual propagation of the new cultivar by hot scion grafting and chip budding has been determined that the characteristics are stable and are reproduced true to type in successive generations.

SUMMARY OF THE INVENTION

The following traits have been repeatedly observed and represent the characteristics of the new cultivar, which in combination distinguish 'Hibbard' as a new distinct cultivar of *Maclura.*

1. 'Hibbard' exhibits a rapid growth habit, an average of 60 cm a year.
2. 'Hibbard' exhibits no fruit production.
3. 'Hibbard' exhibits large glossy foliage.
4. 'Hibbard' exhibits thornless branches.

'Hibbard' can be most closely compared to the *Maclura pomifera* cultivars 'Wichita' (not patented) and 'White Shield' (not patented). Both 'Wichita' and 'White Shield' are similar to 'Hibbard' in being thornless and fruitless. Both 'Wichita' and 'White Shield' differ from 'Hibbard' in having leaf surfaces that are less glossy, less branching at a younger age, and slower growth rates.

BRIEF DESCRIPTION OF THE DRAWINGS

The accompanying color photographs illustrate the overall appearance and distinct characteristics of the new *Maclura*. The photographs were taken of the original 14-year-old tree of 'Hibbard' as growing in the landscape in Wamego, Kansas.

The photograph in FIG. 1 provides a view of the plant habit of 'Hibbard'.

Figure 1:
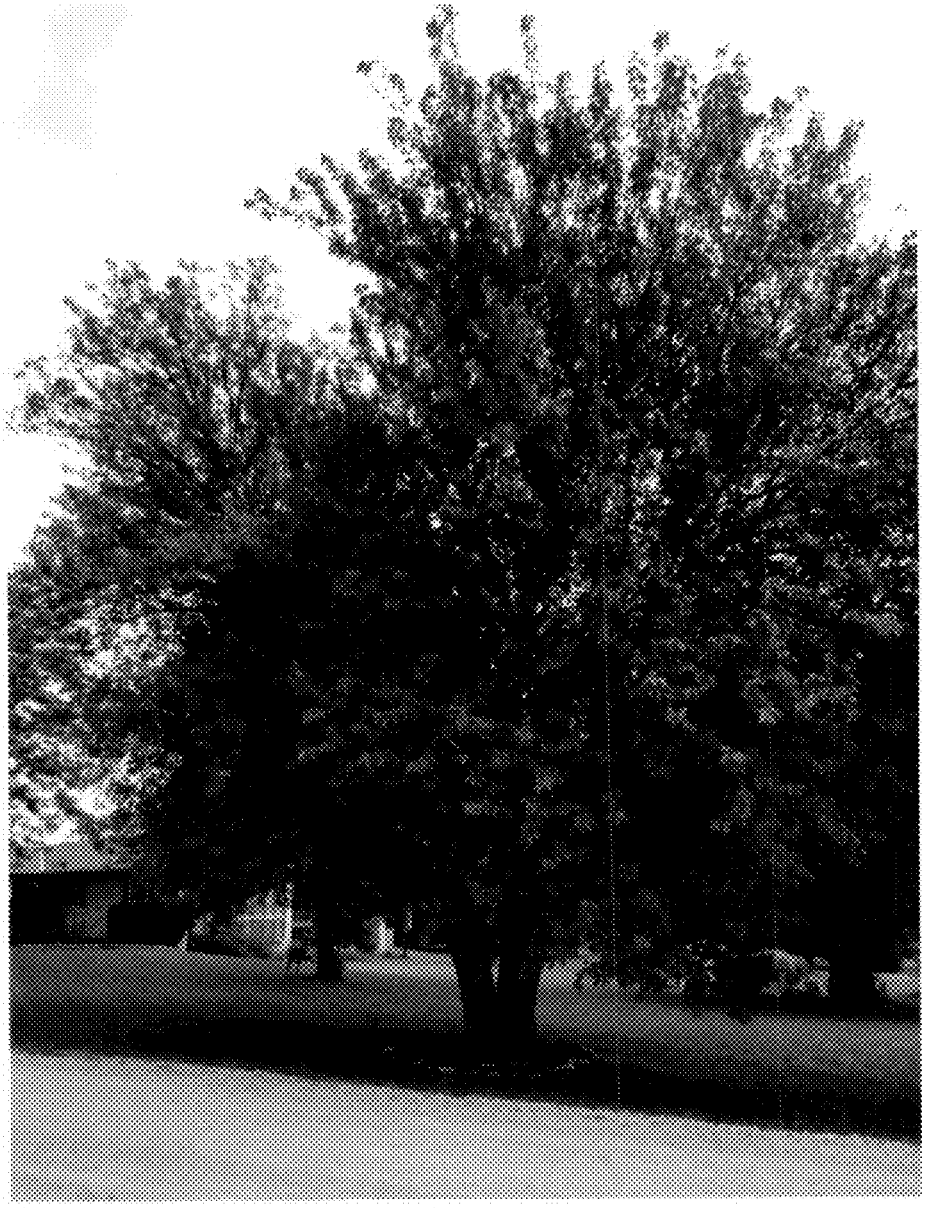
Figure 2:
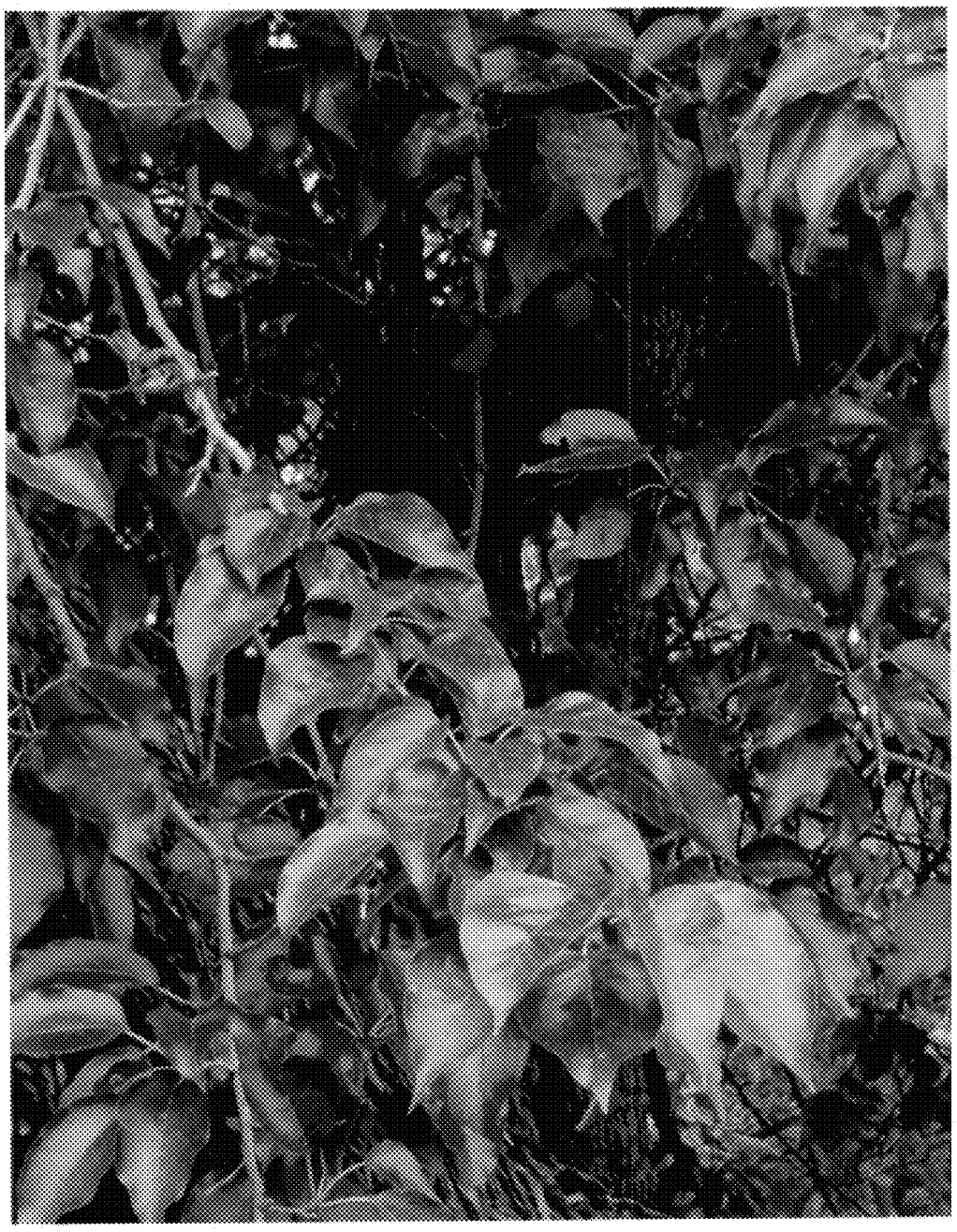

The photograph in FIG. 2 provides a close-up view of the foliage of 'Hibbard'.

The colors in the photographs are as close as possible with the digital photography techniques available, the color values cited in the detailed botanical description accurately describe the colors of the new *Maclura.*

DETAILED BOTANICAL DESCRIPTION

The following is a detailed description of 6-month-old trees of the new cultivar as grown outdoors in 2-quart containers in Boring, Oregon. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Early summer in Kansas.
*Plant type.*—Deciduous tree.
*Plant habit.*—Upright, uniform, fast growing.
*Height and spread.*—Average of 27 cm in height and 20 cm in diameter as six-month- old trees grown in containers, up to 12.2 m in height and 6 m in width when mature in the landscape.
*Cold hardiness.*—At least in U.S.D.A. Zone 4.

*Diseases and pests*.—Have been observed to be disease free, however no specific resistance to any disease has been identified, no resistance or susceptibility to pests has been observed.

*Root description*.—Fibrous, freely branched, 199A and 199B in color.

*Propagation*.—Grafting in winter preferred, ship budding is possible in summer.

*Root development*.—8 weeks for a graft to take after grafting onto rootstock.

*Growth rate*.—High.

Branch description:

*Shape*.—Rounded.

*Branch color*.—Young; 144A, mature; 143A, older wood, bark; a blend of 195A and 198C, occasional blotches and streaks of N199B.

*Branch size*.—Main; 16 cm in height, 6 mm in diameter, lateral; 13 cm in length, 2 mm in diameter.

*Branch surface*.—Thornless, young and mature; slightly glossy, moderately covered with tiny stiff pubescent hairs that match the branch surface, older wood, bark; matte and smooth, slightly rugose.

*Branch strength*.—Main; very strong, lateral; flexible, moderately strong.

*Branching habit*.—Main; 1, lateral; 3 per main branch.

Foliage description:

*Leaf shape*.—Elliptical.

*Leaf division*.—Simple.

*Leaf base*.—Cuneate.

*Leaf apex*.—Acute.

*Leaf fragrance*.—None.

*Leaf venation*.—Pinnate, upper surface color; outer veins match leaf surface, main and center veins 150B in color, lower surface; 145D in color.

*Leaf margins*.—Entire, very slightly undulate.

*Leaf arrangement*.—Alternate.

*Leaf attachment*.—Petiolate.

*Leaf surface*.—Both surfaces glabrous and slightly glossy.

*Leaf size*.—Average of 7.5 cm in length and 4.5 cm in width.

*Leaf color*.—Young and mature upper surface; a blend of 141A and 144A, young and mature low surface; 138A, fall color; 160A in color on both surfaces.

*Petioles*.—Very slightly flattened in shape, average of 2.5 cm in length, 1 mm in width, color; 149C.

Flower description:

*Inflorescence*.—Typical of the species, flowers are produced in umbel inflorescences that are oval in shape, 2 cm in depth, 1.5 cm in diameter, 6 per branch.

*Lastingness of inflorescence*.—About one month (weather dependent).

*Flowers*.—1.5 mm in diameter and depth, flowers are globular or in short cylindrical clusters, average of 30 per inflorescence, no petals visible for data collection.

*Peduncles*.—3 cm in length, 1 cm in diameter, surface is glabrous, N144A in color.

*Pedicels*.—2 mm in length, 1 mm in diameter, surface is glabrous, 145A in color.

*Sepals*.—Average of 4, 1 mm in length and width, 145A in color.

*Calyx*.—2 mm in diameter, 1 mm in depth.

*Reproductive organs*.—Average of 4 stamens; 1.5 mm in length, 202A in color, anthers; 0.5 mm in diameter, 11B in color, pollen; none observed, ovary; none observed, pistil; none observed.

Fruit, and seed description: Has been observed to not produce seed or fruit.

It is claimed:

1. A new and distinct cultivar of *Maclura* tree named 'Hibbard' as herein illustrated and described.

* * * * *